United States Patent [19]

Mueller et al.

[11] 4,112,024

[45] Sep. 5, 1978

[54] PHOSPHORYL SULFENYL CHLORIDE OLEFIN ADDUCTS

[75] Inventors: Wolfgang H. Mueller, Neuallschwil, Switzerland; Alexis A. Oswald, Mountainside, N.J.; Daniel N. Hall, Shaker Heights, Ohio

[73] Assignee: Exxon Research & Engineering Co., Linden, N.J.

[21] Appl. No.: 759,060

[22] Filed: Jan. 13, 1977

Related U.S. Application Data

[63] Continuation-in-part of Ser. No. 594,593, Jul. 10, 1975, Pat. No. 4,003,939, which is a continuation of Ser. No. 836,128, Jun. 24, 1969, abandoned, which is a continuation-in-part of Ser. No. 595,559, Oct. 28, 1966, abandoned.

[51] Int. Cl.$^2$ ............................................. C07F 9/165
[52] U.S. Cl. ................................... 260/956; 260/957; 260/963
[58] Field of Search ................................. 260/971, 956

[56] References Cited

U.S. PATENT DOCUMENTS 3,081,329   3/1963   Vegter ............................. 260/971 X

OTHER PUBLICATIONS

Muller et al., "J. Org. Chem." vol. 31, pp. 3537–3543 (1966).
Michalski et al., 37 Chem. Abst." vol. 51, p. 2535, 1957.

*Primary Examiner*—Anton H. Sutto
*Attorney, Agent, or Firm*—Juseph J. Allocca

[57] ABSTRACT

Phosphorylsulfenyl halides are added to monoolefins, multiolefins, conjugated multiolefins and acetylenic compounds. 1,2-Markownikov oriented adducts are the principle products when conjugated diolefins are employed as the starting feedstock. Anti-Markownikov adducts are obtained as major products when unsymmetrical monoolefins and nonconjugated multiolefins are used as the starting material. The addition reactions are conducted at low temperatures. The materials which are obtained are of interest as pesticides and as intermediates in the synthesis of pesticides.

11 Claims, No Drawings

PHOSPHORYL SULFENYL CHLORIDE OLEFIN ADDUCTS

CROSS-REFERENCE TO RELATED APPLICATIONS

This application is a continuation-in-part of Ser. No. 594,593 filed July 10, 1975, now U.S. Pat. No. 4,003,939, which is a continuation under Rule 60 of Ser. No. 836,128, now abandoned, filed June 24, 1969, which is a continuation-in-part of Ser. No. 595,559, now abandoned, filed Oct. 28, 1966.

BACKGROUND OF THE INVENTION

I. Field of the Invention

Phosphorylsulfenyl halides are added to monoolefins, multiolefins, conjugated multiolefins and acetylenic compounds. 1,2-Markownikov oriented adducts are the principle products when conjugated diolefins are employed as the starting feedstock. Anti-Markownikov adducts are obtained as major products when unsymmetrical monoolefins and nonconjugated multiolefins are used as the starting material. The addition reactions are conducted at low temperatures. The materials which are obtained are of interest as pesticides and as intermediates in the synthesis of pesticides.

II. Description of the Prior Art

In accordance with Markownikov's rule, in the addition reaction of two organic molecules, the least hydrogenated carbon atom of one will combine with the most negative element of the other. Therefore, as disclosed by N. Kharasch, Sulfenium Ions and Sulfenyl Compounds, in "Organic Sulfur Compounds," Vol. 1, 1961, pp. 375–396, the reaction between an olefin and a sulfenyl chloride affords Markownikov-oriented products according to the following equation:

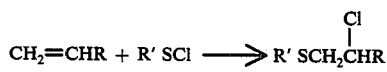

III. Summary of the Invention

It has now been discovered that phosphorylsulfenyl halides and thiophosphorylsulfenyl halides can be added to olefins and acetylenic compounds to form useful adducts. Anti-Markownikov oriented adducts are secured when the sulfenyl halide materials are added to unsymmetrical monoolefins and non-conjugated multiolefins. If, however, a conjugated diolefin is reacted with the sulfenyl halide material, a 1,2-Markownikov oriented adduct is produced. The adducts of the invention are useful as pesticides and as intermediates in the synthesis of pesticides.

Representative reactions contemplated by the instant invention proceed in the following manner:

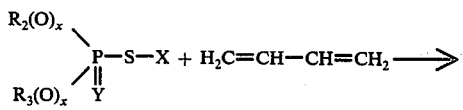

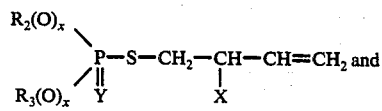

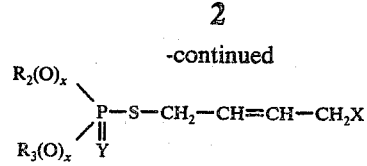

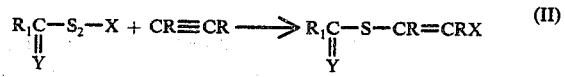

Equation (I) illustrates the reaction of a phosphoryl or thiophosphorylsulfenyl halide with butadiene to secure 1,2 and 1,4-Markownikov oriented products. In reactions of this type, the 1,2-Markownikov oriented product predominates (greater than 50 mole %).

Equation (II) illustrates the reaction of an acylthiosulfenyl halide with an acetylenic compound to form an ethylenically unsaturated adduct product. Phosphoryl or thiophosphorylsulfenyl halides could be substituted for the acylthiosulfenyl halide employed in the reaction. The orientation of the product secured with the reactions based on acetylene depends upon the identity of the acetylenic compound and the type of solvent employed in the reaction. For example, when an alkyl substituted acetylenic compound is employed as a co-reactant, the products are primarily anti-Markownikov oriented. In contrast, when a phenylacetylene is employed as a co-reactant, the products are primarily 1,2-Markownikov oriented.

The sulfenyl halide materials that are employed in reactions with unsaturated organic compounds in accordance with the present invention have the following general formulae:

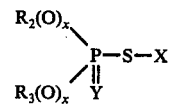

wherein "$x$" is 0 or 1, $R_2$ and $R_3$ are monovalent, substituted or unsubstituted, hydrocarbyl radicals having from 1 to 30 carbon atoms, preferably (a) a $C_1$ to $C_{30}$, more preferably a $C_1$ to $C_{14}$ and most preferably a $C_1$ to $C_6$ alkyl radical, for example methyl, propyl, t-butyl, cyclohexyl, 4-ethyldodecyl, 3-butoxyheptyl, 4-chlorohexyl, decyl, 2-t-butyl-4-propylthio-nonyldecane, etc.; (b) $C_6$ to $C_{16}$ aryl radicals, e.g., phenyl, thiophenyl, thiazole, etc.; (c) $C_7$ to $C_{30}$, preferably $C_7$ to $C_{16}$, alkylaryl radicals, for example, tolyl, diethylphenyl, 2-ethyl-4-chlorophenyl, diethylnaphthyl, nonyl-phenyl, etc.; (d) $C_7$ to $C_{30}$, preferably $C_7$ to $C_{16}$ aralkyl radicals, for example, benzyl, phenylethyl, dibutylbenzyl, 2-ethyl-3-butoxybenzyl, etc.; and (e) their halo, particularly chloro and bromo, alkylthio-(radicals having from 1 to 10 carbon atoms), alkoxy-(radicals having from 1 to 10 carbon atoms), acyl and carboalkoxy-(radicals having from 1 to 10 carbon atoms) substituted derivatives; Y is a sulfur or oxygen atom and X is a halogen atom, e.g., chlorine and bromine atoms. Most preferably, $R_2$ and $R_3$ are methyl, ethyl or phenyl radicals, Y is an oxygen atom and X is a chlorine atom.

Representative examples of useful phosphorylsulfenyl halides and thiophosphorylsulfenyl halides include: O,O'-dimethylphosphorylsulfenyl chloride, O,O'-diethylthiophosphorylsulfenyl bromide, O,O'-diphenylphosphorylsulfenyl bromide, O,O'-dibenzylphosphorylsulfenyl bromide, O,O'-diphenylethylphosphorylsulfenyl chloride, O,O'-di-t-butylthiophosphorylsulfenyl bromide, diphenylphosphorylsulfenyl chloride, O-ethyl-phenylphosphorylsulfenyl chloride, didodecylphosphorylsulfenyl chloride, O-chlorophenyl-chloromethylphosphorylsulfenyl chloride, dibenzylphosphorylsulfenyl chloride, diphenylethylphosphorylsulfenyl chloride, ditolylphosphorylsulfenyl chloride, etc.

The unsaturated hydrocarbons employed to prepare the compositions of the instant invention are, in general, $C_2$ to $C_{50}$ hydrocarbons containing at least one acetylenic triple bond, $C_3$ to $C_{50}$ hydrocarbons containing at least one non-aromatic ethylenic double bond and analogs thereof. Useful acetylenic compounds include: $C_2$ to $C_{10}$, preferably $C_2$ to $C_6$ alkyl acetylenes, such as acetylene, methylacetylene, butyne-1, butyne-2, hexyne-1, octyne-3, etc.; phenyl acetylene; $C_9$ to $C_{14}$ aralkyl acetylene compounds, e.g. 3-phenylpropyne-1, 4-phenylbutyne-2, 3-phenylhexyne-1, etc.; and $C_9$ to $C_{14}$ alkyl substituted phenylacetylenes, such as 3-t-butylphenylacetylene, 2,4-diethylphenylacetylene, 2-methylphenylacetylene, 4-octylphenylacetylene, etc.

Preferably, the ethylenically unsaturated hydrocarbons are (a) $C_3$ to $C_{50}$, more preferably $C_3$ to $C_{30}$, and most preferably $C_3$ to $C_{13}$ acyclic unsymmetrical monoolefins, that is terminal olefins or internal olefins wherein the carbon atoms having the ethylenic site of unsaturation contain differing numbers of hydrogen atoms, for example, propylene, isobutylene, butene-1, dodecene-1, triacontene, hexene-1, 6-methylthiohexene-1, 8-carboethoxyoctene-1, 12-chlorododecene-1, etc.; (b) $C_4$–$C_{14}$ conjugated and nonconjugated acyclic aliphatic multiolefins, preferably diolefins, e.g., 1,5-hexadiene, 1,6-octadiene, trivinylcyclohexane, butadiene, isoprene, chloroprene, cyanoprene, piperylene, fluoroprene, 2,5-dimethyl-2,4-hexadiene, dimethylbutadiene, etc.; (c) $C_3$–$C_{12}$ unsymmetrical alicyclic aliphatic monoolefins, for example, 1-methylcyclopentene, 1-ethylcyclooctene, 1-butylcycloheptene, etc.; (d) $C_3$ to $C_{12}$ alicyclic aliphatic diolefins, such as 1-methylcyclododecadiene-1,5, cyclododecadiene-1,3, 1-ethylcyclooctadiene-1,4, cyclopentadiene, methylcyclopentadiene, dimethyldicyclopentadiene, etc.; (e) $C_9$ to $C_{16}$ alkenyl substituted aromatics, said alkenyl substitution preferably having the site of unsaturation located on the terminal carbon atom and having from 3 to 10 carbon atoms, such as allyl benzene, 5-phenylhexene-1, allyl-naphthylene, etc.; and (f) halogen, preferably chlorine, substituted derivatives thereof. Most preferably, the unsaturated hydrocarbons are straight chain terminal monoolefins or $C_4$ to $C_{10}$ conjugated acyclic diolefins. The olefinic and acetylenic compounds may be substituted or unsubstituted; however it is generally preferred that they be unsubstituted. Conjugated acyclic dienes, such as butadiene and chloroprene, are of particular interest because new products are formed therefrom which have higher reactivity than simple dienes. The preferred olefinic feedstocks have from 3 to 6 carbon atoms.

The addition reactions occur at a temperature of from $-100°$ C. to $+100°$ C., preferably below about $0°$ C. and the pressure of the reaction should be maintained at from 5 to 140 psia, preferably at atmospheric pressure. In the addition reaction between a sulfenyl halide and a monoolefin, the reactants should be present in a mole ratio of sulfenyl halide to unsaturate, from 5:1 to 1:10, preferably from 1.1:1 to 1:1.1. If a diolefin or multiolefin is employed, for example, a conjugated diene such as butadiene, a 3–10 fold, preferably 2–5 fold, excess of the unsaturate should be employed. In reactions involving acetylenic compounds, the molar ratio of sulfenyl halide to acetylenic compound within the reaction zone should be maintained between 50:1 to 2:1, preferably from 5:1 to 2:1. Preferably, the reactants are brought together in the liquid state.

If liquid olefinic or acetylenic unsaturates are utilized, the sulfenyl halide may be added slowly, preferably dropwise, to an excess of unsaturate to control the temperature. The reaction temperature is preferably maintained at less than $0°$ C., for a period of from 0.1 to 5 hours. After the reaction is complete, the mixture is brought slowly to room temperature and the excess unsaturate and solvent are removed under reduced pressure. The crude product may be distilled under high vacuum and low temperatures.

Sulfenyl halides may be reacted with gaseous olefins by bubbling the gas through the sulfenyl halide. If has been discovered, however, that better yields are obtained if the sulfenyl halide is dropped slowly into a solution of the gaseous olefins in a suitable solvent such as methylene chloride, carbon tetrachloride, chloroform, ethyl ether, dimethyl sulfide, hydrocarbons or the like. The volume ratio of solvent to reactant, for reactions involving either gaseous or normally liquid unsaturates, may range from 0.5 to 20, preferably 1 to 10.

The novel compositions of this invention include the phosphoryl and thiophosphoryl adducts of open-chain conjugated dienes having the general formulae:

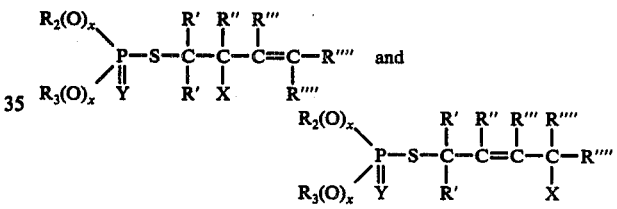

wherein $x$, $R_2$, $R_3$, $X$ are defined as above and $R'$, $R''$, $R'''$, and $R''''$ represent the residues of the starting $C_4$ to $C_{14}$ acyclic conjugated diolefin. More particularly, $R'$, $R''$, $R'''$ and $R''''$ denote either hydrogen atoms, chlorine atoms or monovalent lower alkyl radicals, the sum of the carbon atoms of all of the lower alkyl radicals not exceeding about 10 carbon atoms, preferably not exceeding about 6 atoms.

Other novel compositions include the monoadducts of phosphoryl sulfenyl halides and thiophosphorylsulfenyl halides with a monoacetylenic compounds, such monoadducts having the general formula

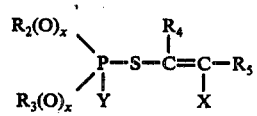

wherein $x$, $R_2$, $R_3$, $Y$ and $X$ are as defined above and $R_4$ and $R_5$ are the residues of the starting acetylenic compound. Preferably, $R_4$ and $R_5$ are hydrogen atoms, monovalent alkyl radicals having from 1 to 8 carbon atoms, preferably 1 to 4 carbon atoms (the sum of the carbon atoms of the $R_4$ and $R_5$ alkyl chains not exceeding about 8, preferably not exceeding about 4 carbon atoms), phenyl radicals, alkyl substituted phenyl radicals, and phenyl substituted alkyl radicals having from 7 to 16 carbon atoms.

Anti-Markownikov oriented adducts produced by the addition of thiophosphorylsulfenyl halides or phosphorylsulfenyl halides to terminal olefins are also included. Such adducts have the following general formula:

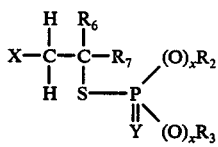

wherein $x$, $R_2$, $R_3$, X and Y are as previously defined, and $R_6$ and $R_7$ are the residues of the starting terminal aliphatic monoolefin. Specifically, $R_6$ is a $C_1$ to $C_{12}$ alkyl radical, a phenyl radical, or a $C_7$ to $C_{14}$ aralkyl radical, and $R_7$ is a hydrogen radical or a hydrocarbyl radical of the type described with reference to $R_6$.

The pesticidal compositions prepared with the compositions of the present invention can be employed either in solid or liquid form. When used in solid form they may be reduced to an impalpable powder and applied as an undiluted dust or mixed with a solid carrier such as clay, talc and bentonite, as well as other inert carriers known in the art. The pesticidal compositions can also be applied as an atomized spray or in a liquid carrier either as the solution in a solvent or as an emulsion in a nonsolvent such as water. In the diluted solid or liquid form the compositions of the instant invention can be employed in an amount of from between 0.01 and about 5 weight percent based on the inert carrier. Typical liquid solvents include such compounds as acetone, ethyl alcohol, benzene, naphtha and the like. Suitable wetting agents such as long chain alcohols, sulfonated amide and ester derivatives, sulfonated aromatic and mixed alkyl aryl derivatives, ester or fatty acids and petroleum sulfonates of $C_{10}$ to $C_{20}$ nonionic emulsifying agents can also be employed in preparing the pesticidal compositions. The compounds of this invention can also be admixed with carriers that are themselves pesticides.

The invention is illustrated by the following examples.

EXAMPLE 1

O,O'-dimethylphosphorylsulfenyl chloride was prepared in high yield (greater than 90%) by reacting trimethylphosphorothionate with a molar equivalent of sulfuryl chloride. The reaction temperature was maintained below 0° C. The removal of the gaseous products under high vacuum afforded the phosphorylsulfenyl chloride. This procedure was developed after it was found that considerably lower yields and no high product purity resulted from preparation of the sulfenyl chloride in benzene with a final vacuum distillation. The O,O'-dimethylphosphorylsulfenyl chloride was then reacted with ethylene, propylene, pentene-1, butadiene, isoprene, methylacetylene and allene. Reactions involving liquid unsaturates were performed in accordance with the conditions disclosed in Example 2 and the reactions involving gaseous unsaturates were performed in accordance with the description in Example 3.

EXAMPLE 2

The O,O'-dimethylphosphorylsulfenyl chloride prepared in accordance with the description of Example 1 was added dropwise to a 5 molar excess of the liquid unsaturate (equimolar in the case of olefins) contained in a three-neck flask fitted with a thermometer, a condenser with nitrogen purge, an addition funnel and a magnetic stirrer. The reaction temperature was maintained below 0° C. with an ice-salt bath. After the addition was complete, the reaction mixture was brought slowly to room temperature. The excess unsaturate was removed under reduced pressure and the remaining oil taken up in ether. The ethereal solution was washed with 5% sodium bicarbonate solution until basic and then with water until neutral and was then dried over magnesium sulfate. Then the ether was removed under reduced pressure. The remaining crude product was then distilled under high vacuum using an apparatus with a heated, packed column and a short-path condenser.

EXAMPLE 3

For reactions involving gaseous unsaturates, 100 milliliters of dried methylene chloride were placed in a 250 milliliter, four-neck flask fitted with a thermometer, a condenser with nitrogen purge, a dropping funnel with glass tubing extending below the surface of the methylene chloride. A 5 molar excess of the gaseous unsaturate (equimolar amounts for olefin reactions) was condensed into the flask which was kept in a dry ice-isopropanol bath. The appropriate amount of O,O'-dimethylphosphorylsulfenyl chloride was added slowly to the unsaturate-methylene chloride solution. After the addition was complete the reaction mixture was allowed to come slowly to room temperature and worked up as described in the previous example.

EXAMPLE 4

All of the products prepared in accordance with Example 2 and Example 3 were analyzed by G.L.C. and N.M.R. Yields were calculated from an analysis of the crude products. As is shown in Table I, a major proportion of the anti-Markownikov oriented products, labeled "Structure I," was produced in case of olefins. Decomposition during distillation diminished the yields. All distilled products were also analyzed by N.M.R. and G.L.C.

TABLE I
O,O'-DIMETHYLPHOSPHORYLSULFENYL CHLORIDE-UNSATURATE MONO-ADDITIONS
AND SOME PHYSICAL-ANALYTICAL DATA OF THE PRODUCTS
$(CH_3O)_2P(O)SR$

| Olefin, 5 mole per Mole Sulfenyl Chloride | Yield[a], % | Selectivity for Adduct[a] I:II | Structure I R | Structure II R | Summary Formula | B.P. Uncorr ° C. (mm.) |
|---|---|---|---|---|---|---|
| Ethylene | 25 | 100g | —$CH_2CH_2Cl$ | | $C_4H_{10}O_3OSCl$ | 82.5 (0.30) |
| Propylene | 29 | 51:49 | —$CHCH_2Cl$<br>$\|$<br>$CH_3$ | —$CH_2CHCH_3$<br>$\|$<br>$Cl$ | $C_5H_{12}O_3PSCl$ | 83.5 (0.30) |

TABLE I-continued
O,O'-DIMETHYLPHOSPHORYLSULFENYL CHLORIDE-UNSATURATE MONO-ADDITIONS AND SOME PHYSICAL-ANALYTICAL DATA OF THE PRODUCTS
$(CH_3O)_2P(O)SR$

| Olefin, 5 mole per Mole Sulfenyl Chloride | Yield[a], % | Selectivity for Adduct[a] I:II | Structure I R | Structure II R | Summary Formula | B.P. Uncorr ° C. (mm.) |
|---|---|---|---|---|---|---|
| Pentene-1 | 71[b] | 65:35 | —CHC$_3$H$_7$<br>\|<br>CH$_2$Cl | —CH$_2$CHC$_3$H$_7$<br>\|<br>Cl | C$_7$H$_{16}$O$_3$PSCl | 94 (0.004) |
| Butadiene | 97 | 73:27 | —CH$_2$CHCH=CH$_2$<br>\|<br>Cl | —CH—CH=CH$_2$<br>\|<br>CH$_2$Cl | C$_6$H$_{12}$O$_3$PSCl | 104–106 (0.01) |
| Isoprene | 59[b] | 65:35 | —CH$_2$CH—C=CH$_2$<br>\| \|<br>Cl CH$_3$ | —CHC(CH$_3$)=CH$_2$<br>\|<br>CH$_2$Cl | C$_7$H$_{14}$O$_3$PSCl | 117–120 (0.01) |
| Methyl Acetylene | 55[b] | 71:29 | —C=C—H<br>\| \|<br>CH$_3$ Cl | —C=C—Cl<br>\| \|<br>CH$_3$ H | C$_5$H$_{10}$O$_3$PSCl | 74–77 (0.22) |
| Allene | 53[b] | 100 | —C=CH$_2$<br>\|<br>CH$_2$Cl | | C$_5$H$_{10}$O$_3$PSCl | 84.5–86 (0.20) |

[a]Based on the weight and semiquantitative N.M.R. analysis of the crude reaction products because of decomposition of adducts during distillation.
[b]Theoretical yield is based on quantity of S=P(OCH$_3$)$_3$ used because the sulfenyl chloride was not isolated.

EXAMPLE 5

The O,O'-dimethylphosphorylsulfenyl chloride adducts of ethylene, propylene, butadiene, isoprene, methyl acetylene and allene were tested for their insecticidal activity. These tests were carried out by the Wisconsin Alumni Research Foundation. An acetone solution of the individual adducts was dispersed in distilled water with an emulsifier to give spray emulsions of 0.05% adduct. These emulsions were used in standard laboratory insecticidal tests as is shown in Table II. The materials prepared in accordance with this invention were at a concentration of 0.05% effective in killing house flies and Mexican bean beetles. They were of course somewhat less effective at lower concentrations.

EXAMPLE 6

The adducts described in Example 5 were also tested as nematocides. Meloidigyne species, nematodes were reared in tomato plant-soil medium. Soil for test purposes was innoculated with infected soil and root knots. In the modified test for the compounds with high vapor pressure, 3 milliliters acetone solution of the sample was inserted in the soil and the soil was kept sealed for 5 days; then ball milled for 5 minutes and then held for an additional 2 days before plotting and planting of tomato plants. In a routine test, the same procedure was used without the 5 day sealing. One pint paper pots were used for each treatment with one tomato transplant per pot. After 3 to 4 weeks under artificial light and overhead irrigation the roots of the plants were examined to determine the degree of root knot formation. Innoculated controls normally had about 50 to 100 root knots

TABLE II

| Compounds | Isomor, Ratio % | Conc., % | House flies 24 hrs. | Mexican Bean Beetles 48 hrs. | Pea Aphids Contact 48 hrs. | Pea Aphids Systemic 5 Days | Mites Contact 5 Days |
|---|---|---|---|---|---|---|---|
| (CH$_3$O)$_2$P(O)SCH$_2$CH$_2$Cl | | 0.05 | 100 | 100 | 20 | 100 | 100 |
| (CH$_3$O)$_2$P(O)SCH$_2$CHCH$_3$<br>     \|<br>     Cl | 49 | 0.05 | 70 | 50 | 20 | 80 | 69 |
| (CH$_3$O)$_2$P(O)SCHCH$_2$Cl<br>     \|<br>     CH$_3$ | 51 | | | | | | |
| (CH$_3$O)$_2$P(O)SCH$_2$CHCH=CH$_2$<br>     \|<br>     Cl | 73 | 0.05 | 100 | 40 | 50 | 0 | 61 |
| (CH$_3$O)$_2$P(O)SCH$_2$CH=CH—CH$_2$Cl | 27 | | | | | | |
| (CH$_3$O)$_2$P(O)SCH$_2$C—C=CH$_2$<br>     \| \|<br>     Cl CH$_3$ | 65 | 0.05 | 80 | 100 | 80 | 0 | 47 |
| (CH$_3$O)$_2$P(O)SCH—C=CH$_2$<br>     \|<br>     CH$_2$Cl | 35 | 0.005 | — | 50 | — | — | 0 |
| (CH$_3$O)$_2$P(O)SCH—C=CH$_2$<br>     \|<br>     CH$_3$ | | | | | | | |
| (CH$_3$O)$_2$P(O)SC=CHCl<br>     \|<br>     CH$_3$ | | 0.05 | 96 | 100 | 40 | 20 | 39 |
| (CH$_3$O)$_2$P(O)SC=CH$_2$<br>     \|<br>     CH$_2$Cl | | 0.05 | 12 | 100 | 40 | 0 | 65 | per plant. Percent control was determined by comparison of the root knots on treated and untreated tomato plants. As is shown in Table III, the adducts tested demonstrated nematocidal activity at a concentration of 40 lbs. per acre.

TABLE III

| Compound | Isomer % | Rate of Application Lb./Acre | Control of Nematodes,% | |
|---|---|---|---|---|
| | | | Modified Test | Routine Test |
| $(CH_3O)_2P(O)-SCH_2CHCH_3$ <br> $\ \ \ \ \ \ \ \ \ \ \ \ \ \ \ \ \ \ \ \ \ \ \ \ |$ <br> $\ \ \ \ \ \ \ \ \ \ \ \ \ \ \ \ \ \ \ \ \ \ \ \ Cl$ | 49 | | | |
| | | 40 | 20 | — |
| $(CH_3O)_2P(O)-SCHCH_2Cl$ <br> $\ \ \ \ \ \ \ \ \ \ \ \ \ \ \ \ \ \ \ \ \ \ |$ <br> $\ \ \ \ \ \ \ \ \ \ \ \ \ \ \ \ \ \ \ \ \ \ CH_3$ | 51 | | | |
| $(CH_3O)_2P(O)-SCH_2CHCH=CH_2$ <br> $\ \ \ \ \ \ \ \ \ \ \ \ \ \ \ \ \ \ \ \ \ \ \ \ \ \ \ \ \ \ \ \ |$ <br> $\ \ \ \ \ \ \ \ \ \ \ \ \ \ \ \ \ \ \ \ \ \ \ \ \ \ \ \ \ \ \ Cl$ | 73 | | | |
| | | 40 | 56 | — |
| $(CH_3O)_2P(O)-SCHCH=CH_2$ <br> $\ \ \ \ \ \ \ \ \ \ \ \ \ \ \ \ \ \ \ \ \ \ |$ <br> $\ \ \ \ \ \ \ \ \ \ \ \ \ \ \ \ \ \ \ \ CH_2Cl$ | 27 | | | |
| $CH_3C(O)-S_2CH_2CHCH_3$ <br> $\ \ \ \ \ \ \ \ \ \ \ \ \ \ \ \ \ \ \ \ \ |$ <br> $\ \ \ \ \ \ \ \ \ \ \ \ \ \ \ \ \ \ \ \ Cl$ | 40 | | | |
| | | 40 | 50 | — |
| $CH_3C(O)-S_2CH(CH_3)CH_2$ <br> $\ \ \ \ \ \ \ \ \ \ \ \ \ \ \ \ \ \ \ \ \ \ \ \ \ \ \ \ \ \ \ |$ <br> $\ \ \ \ \ \ \ \ \ \ \ \ \ \ \ \ \ \ \ \ \ \ \ \ \ \ \ \ \ \ \ Cl$ | 60 | | | |

EXAMPLE 7

O,O'-dimethylphosphorylsulfenyl bromide is added, following the procedure of Example 2, to a molar excess of heptene-1. A product composed predominantly of the anti-Markownikov adduct is thus obtained.

EXAMPLE 8

O,O'-diisopropylphosphorylsulfenyl chloride and 1,5 hexadiene are reacted following the general procedure of Example 2. A large proportion of the crude product recovered from the reaction is composed of the anti-Markownikov oriented adduct.

EXAMPLE 9

O,O'-dicyclohexylthiophosphorylsulfenyl chloride is reacted with 1-methyl-cyclohexene at a temperature of about −15° C. The reaction conditions and equipment employed are the same as those employed in Example 2. After about 4 hours of reaction time, a high proportion of anti-Markownikov adduct is obtained.

EXAMPLE 10

Diphenylphosphorylsulfenyl chloride is reacted with butadiene in the manner described in Example 3 to yield major amounts of the corresponding Markownikov type 1,2-monoadduct.

What is claimed is:

1. Markownikov oriented adduct materials having the formula:

$$\begin{array}{c} R_2(O)_x \\ \phantom{R_2(O)_x} \diagdown \\ \phantom{R_2(O)_x \diagdown} P-S-\underset{R'}{\underset{|}{C}}-\underset{X}{\underset{|}{C}}-\underset{R'''}{\underset{|}{C}}=\underset{R''''}{\underset{|}{C}}-R'''' \\ \phantom{R_2(O)_x} \diagup \| \\ R_3(O)_x \phantom{\diagup} Y \end{array}$$

and $$\begin{array}{c} R_2(O)_x \\ \phantom{R_2(O)_x} \diagdown \\ \phantom{R_2(O)_x \diagdown} P-S-\underset{R'}{\underset{|}{C}}-\underset{R'}{\underset{|}{C}}=\underset{R'''}{\underset{|}{C}}-\underset{X}{\underset{|}{C}}-R'''' \\ \phantom{R_2(O)_x} \diagup \| \\ R_3(O)_x \phantom{\diagup} Y \end{array}$$

wherein $x$ is 1, Y is O, $R_2$ and $R_3$ are methyl and or ethyl, X is Cl, R', R", R''' and R'''' are selected from the group of H, methyl and chlorine.

2. The compositions of claim 1 wherein X is a chlorine atom and Y is an oxygen atom.

3. The composition of claim 2 wherein R', R", R''' and R'''' are hydrogen atoms.

4. Markownikov oriented adduct material having the formula:

$$(CH_3O)_2P(O)SCH_2\underset{|}{\underset{Cl}{C}}HCH=CH_2$$

and $$(CH_3O)_2P(O)SCH_2CH=CH-CH_2Cl$$

5. A method for obtaining major amounts of anti-Markownikov addition products which comprises adding a sulfenyl halide having the general formula:

$$\begin{array}{c} R_2(O)_x \\ \phantom{R_2(O)_x} \diagdown \\ \phantom{R_2(O)_x \diagdown} P-S-X \\ \phantom{R_2(O)_x} \diagup \| \\ R_3(O)_x \phantom{\diagup} Y \end{array}$$

wherein $x$ is 0 or 1, $R_2$ and $R_3$ are monovalent radicals selected from the group consisting of $C_1$–$C_{30}$ alkyl radicals, $C_6$–$C_{16}$ aryl radicals, $C_7$–$C_{30}$ alkylaryl radicals, $C_7$–$C_{30}$ aralkyl radicals and the halo, alkylthio, alkoxy and acyl and carboalkoxy derivatives thereof, Y is a sulfur or oxygen atom and X is a halogen atom to an unsaturated hydrocarbon selected from the group consisting of $C_3$–$C_{50}$ acrylic unsymmetrical monoolefins, $C_4$–$C_{14}$ acyclic aliphatic nonconjugated multiolefins, $C_3$–$C_{12}$ unsymmetrical alicyclic aliphatic monoolefins, $C_5$–$C_{12}$ alicyclic aliphatic nonconjugated diolefins, $C_9$–$C_{16}$ alkenyl substituted aromatic compounds, said alkenyl substituent having from 3 to 10 carbon atoms, and halogen substituted derivatives thereof, for a time sufficient to recover the addition product containing major amounts of the anti-Markownikov adduct.

6. The process of claim 5 wherein said unsaturated hydrocarbon is a $C_4$–$C_{14}$ acyclic conjugated aliphatic diolefin and the product recovered is a 1,2-Markownikov oriented adduct.

7. The process of claim 5 wherein said unsaturated hydrocarbon is a $C_3$–$C_{14}$ terminal monoolefin and an anti-Markownikov oriented adduct is recovered.

8. The process of claim 5 wherein said addition is conducted at a temperature below about 0° C.

9. The process of claim 5 wherein X is chlorine.

10. The process of claim 5 wherein Y is oxygen.

11. A method for obtaining Markownikov monoaddition products which comprises adding a sulfenyl halide having the general formula:

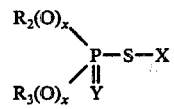

wherein $x$ is 0 or 1, $R_2$ and $R_3$ are monovalent radicals selected from the group consisting of $C_1$–$C_{30}$ alkyl radicals, $C_6$–$C_{16}$ aryl radicals, $C_7$–$C_{30}$ alkylaryl radicals, $C_7$–$C_{30}$ aralkyl radicals and the halo, alkylthio, alkoxy and acyl and carboalkoxy derivatives thereof, Y is a sulfur or oxygen atom and X is a halogen atom to a $C_4$–$C_{14}$ acyclic conjugated aliphatic diolefin for a time sufficient to recover the monoaddition product.

* * * * *